(12) United States Patent
    Alshareef et al.

(10) Patent No.: US 12,415,057 B2
(45) Date of Patent: Sep. 16, 2025

(54) ULTRASOUND-BASED SHUNT FLOW DETECTION

(71) Applicant: MUSC Foundation for Research Development, Charleston, SC (US)

(72) Inventors: Mohammed Alshareef, Charleston, SC (US); Ramin Eskandari, Charleston, SC (US); Joseph Tyler Vasas, North Charleston, SC (US)

(73) Assignee: MUSC Foundation for Research Development, Charleston, SC (US)

( * ) Notice: Subject to any disclaimer, the term of this patent is extended or adjusted under 35 U.S.C. 154(b) by 618 days.

(21) Appl. No.: 17/773,152

(22) PCT Filed: Oct. 30, 2020

(86) PCT No.: PCT/US2020/058220
    § 371 (c)(1),
    (2) Date: Apr. 29, 2022

(87) PCT Pub. No.: WO2021/087264
    PCT Pub. Date: May 6, 2021

(65) Prior Publication Data
    US 2022/0355086 A1    Nov. 10, 2022

Related U.S. Application Data

(60) Provisional application No. 62/928,889, filed on Oct. 31, 2019.

(51) Int. Cl.
    *A61M 27/00*    (2006.01)
    *G01F 1/663*    (2022.01)
(52) U.S. Cl.
    CPC ........... *A61M 27/006* (2013.01); *G01F 1/663* (2013.01); *A61M 2205/332* (2013.01); *A61M 2205/3375* (2013.01); *A61M 2205/3584* (2013.01)

(58) Field of Classification Search
    CPC .......... A61M 27/006; A61M 2205/332; A61M 2205/3375; A61M 2205/3584; G01F 1/663
    See application file for complete search history.

(56) References Cited

U.S. PATENT DOCUMENTS 3,534,739 A * 10/1970 Bryne ..................... A61B 18/02
                                                         222/394
4,043,341 A *  8/1977 Tromovitch ............ B05B 11/06
                                                         606/22
(Continued)

FOREIGN PATENT DOCUMENTS

CA          2971816 A1    12/2017
CN       207591015 U  *   7/2018    .......... A61M 1/0023
(Continued)

OTHER PUBLICATIONS

Aralar, April et al. "Assessment of Ventriculoperitoneal Shunt Function Using Ultrasound Characterization of Valve Interface Oscillation as a Proxy." Cureus vol. 10,2 e2205. 15 pages. Feb. 19, 2018, doi:10.7759/cureus.2205.

(Continued)

*Primary Examiner* — Guy K Townsend
(74) *Attorney, Agent, or Firm* — Riverside Law LLP (57) ABSTRACT

The present invention provides devices and systems for detecting shunt malfunction. The detection devices employ ultrasound instrumentations to evaluate shunt malfunction. The detection devices can be coupled with pumps to provide consistent shunt valve and/or reservoir actuation for reliable readings. The devices can output a determination of a degree of shunt blockage and relative location of shunt blockage.

9 Claims, 8 Drawing Sheets

(56) References Cited

U.S. PATENT DOCUMENTS

| | | | | |
|---|---|---|---|---|
| 4,348,873 A * | 9/1982 | Yamauchi | A61B 18/0218 | 606/20 |
| 4,376,376 A * | 3/1983 | Gregory | F17C 9/00 | 62/48.1 |
| 4,861,331 A | 8/1989 | East | | |
| 5,098,428 A * | 3/1992 | Sandlin | A61B 18/0218 | 62/52.1 |
| 5,344,478 A * | 9/1994 | Zurecki | B22D 27/003 | 75/709 |
| 5,657,000 A * | 8/1997 | Ellingboe | F04B 49/06 | 417/63 |
| 5,685,989 A * | 11/1997 | Krivitski | A61M 1/367 | 210/103 |
| 5,814,040 A * | 9/1998 | Nelson | A61B 18/0218 | 606/2 |
| 5,997,530 A * | 12/1999 | Nelson | A61B 90/04 | 606/2 |
| 6,027,499 A * | 2/2000 | Johnston | A61B 18/0218 | 606/22 |
| 6,171,301 B1 * | 1/2001 | Nelson | A61N 5/062 | 606/9 |
| 6,226,996 B1 * | 5/2001 | Weber | F17C 9/02 | 236/51 |
| 6,248,103 B1 * | 6/2001 | Tannenbaum | A61N 5/062 | 606/9 |
| 6,514,244 B2 * | 2/2003 | Pope | A61B 18/203 | 606/2 |
| 6,635,053 B1 * | 10/2003 | Lalonde | A61B 18/02 | 606/22 |
| 6,764,493 B1 * | 7/2004 | Weber | A61M 37/00 | 451/75 |
| 6,996,951 B2 * | 2/2006 | Smith | B29C 66/242 | 53/469 |
| 7,025,762 B2 * | 4/2006 | Johnston | A61B 34/35 | 606/22 |
| 7,255,693 B1 * | 8/2007 | Johnston | A61B 18/02 | 606/20 |
| 7,273,479 B2 * | 9/2007 | Littrup | A61B 18/02 | 128/898 |
| 7,282,060 B2 * | 10/2007 | DeBenedictis | A61B 18/203 | 606/9 |
| 7,318,821 B2 * | 1/2008 | Lalonde | A61B 18/02 | 606/22 |
| 7,769,469 B2 * | 8/2010 | Carr | A61N 1/403 | 607/101 |
| 7,780,656 B2 * | 8/2010 | Tankovich | A61B 18/0218 | 606/9 |
| 7,921,657 B2 * | 4/2011 | Littrup | F25B 9/02 | 62/64 |
| 8,152,751 B2 * | 4/2012 | Roger | A61M 1/14 | 604/4.01 |
| 8,216,173 B2 * | 7/2012 | Dacey, Jr. | A61B 5/14503 | 604/9 |
| 8,282,593 B2 * | 10/2012 | Dacey, Jr. | A61N 1/205 | 604/9 |
| 8,317,770 B2 | 11/2012 | Miesel | | |
| 8,343,086 B2 * | 1/2013 | Dacey, Jr. | A61M 27/006 | 604/8 |
| 8,366,652 B2 * | 2/2013 | Dacey, Jr. | A61N 5/0624 | 604/9 |
| 8,414,517 B2 * | 4/2013 | Dacey, Jr. | A61N 1/205 | 604/9 |
| 8,591,504 B2 * | 11/2013 | Tin | A61B 18/02 | 606/21 |
| 8,603,020 B2 * | 12/2013 | Roger | A61M 1/14 | 604/4.01 |
| 8,795,217 B2 * | 8/2014 | Roger | A61M 1/3653 | 604/4.01 |
| 8,888,731 B2 * | 11/2014 | Dacey, Jr. | A61L 2/08 | 604/9 |
| 8,920,355 B2 * | 12/2014 | Roger | A61M 1/3653 | 604/6.06 |
| 9,039,648 B2 * | 5/2015 | Kelly | A61M 1/1561 | 604/6.08 |
| 9,089,654 B2 * | 7/2015 | Roger | A61M 1/3656 | |
| 9,138,528 B2 * | 9/2015 | Roger | A61M 1/3607 | |
| 9,138,568 B2 | 9/2015 | Swoboda | | |
| 9,149,648 B2 * | 10/2015 | Dacey, Jr. | A61L 2/08 | |
| 9,352,078 B2 * | 5/2016 | Roger | A61M 1/3607 | |
| 9,550,020 B2 * | 1/2017 | Kelly | A61M 1/1633 | |
| 9,687,670 B2 * | 6/2017 | Dacey, Jr. | A61N 5/0601 | |
| 9,872,972 B2 | 1/2018 | Soares | | |
| 9,950,105 B2 * | 4/2018 | Roger | A61M 1/3653 | |
| 9,974,932 B2 * | 5/2018 | Kim | A61M 27/006 | |
| 10,213,585 B2 | 2/2019 | Soares | | |
| 10,413,654 B2 * | 9/2019 | Funkhouser | A61M 1/3639 | |
| 10,463,778 B2 * | 11/2019 | Roger | A61N 1/00 | |
| 10,478,555 B2 * | 11/2019 | Radojicic | A61M 27/006 | |
| 10,695,484 B1 * | 6/2020 | Radojicic | A61M 39/0208 | |
| 10,772,998 B2 * | 9/2020 | Luxon | A61M 1/63 | |
| 11,103,657 B2 * | 8/2021 | Brown | A61L 2/025 | |
| 11,759,583 B2 * | 9/2023 | Brown | A61L 2/20 | 600/104 |
| 2001/0009997 A1 * | 7/2001 | Pope | A61B 18/203 | 606/2 |
| 2002/0143323 A1 * | 10/2002 | Johnston | A61B 34/35 | 606/22 |
| 2002/0161357 A1 * | 10/2002 | Anderson | A61B 18/203 | 606/17 |
| 2004/0002704 A1 * | 1/2004 | Knowlton | A61N 1/06 | 606/41 |
| 2005/0154380 A1 * | 7/2005 | DeBenedictis | A61B 18/203 | 606/9 |
| 2005/0261753 A1 * | 11/2005 | Littrup | F25B 9/02 | 607/96 |
| 2006/0020239 A1 | 1/2006 | Geiger | | |
| 2006/0235349 A1 | 10/2006 | Osborn | | |
| 2007/0118098 A1 * | 5/2007 | Tankovich | A61B 18/203 | 606/17 |
| 2007/0208293 A1 | 9/2007 | Mansour | | |
| 2007/0276360 A1 * | 11/2007 | Johnston | A61B 18/02 | 606/21 |
| 2008/0071332 A1 * | 3/2008 | Nelson | A61B 18/20 | 607/96 |
| 2008/0119828 A1 * | 5/2008 | Nelson | A61B 18/203 | 606/9 |
| 2008/0173028 A1 * | 7/2008 | Littrup | F25B 9/02 | 62/62 |
| 2008/0195021 A1 * | 8/2008 | Roger | A61M 1/3639 | 604/4.01 |
| 2008/0195060 A1 * | 8/2008 | Roger | A61M 1/3656 | 604/246 |
| 2008/0287943 A1 * | 11/2008 | Weber | A61B 18/14 | 606/41 |
| 2009/0192505 A1 * | 7/2009 | Askew | A61M 16/0463 | 424/9.4 |
| 2010/0057065 A1 * | 3/2010 | Krimsky | A61B 18/0218 | 606/21 |
| 2010/0111837 A1 * | 5/2010 | Boyden | A61K 35/32 | 424/9.1 |
| 2010/0111846 A1 * | 5/2010 | Boyden | A61K 9/1664 | 424/1.29 |
| 2010/0111847 A1 * | 5/2010 | Boyden | A61K 33/00 | 424/9.1 |
| 2010/0111848 A1 * | 5/2010 | Boyden | A61K 31/337 | 424/9.1 |
| 2010/0111849 A1 * | 5/2010 | Boyden | A61K 33/00 | 424/9.1 |
| 2010/0111850 A1 * | 5/2010 | Boyden | A61K 9/1611 | 424/9.1 |
| 2010/0111854 A1 * | 5/2010 | Boyden | A61K 9/007 | 424/1.49 |
| 2010/0111855 A1 * | 5/2010 | Boyden | A61K 9/19 | 514/249 |
| 2010/0111938 A1 * | 5/2010 | Boyden | C07K 16/2842 | 435/395 |
| 2010/0112067 A1 * | 5/2010 | Boyden | C07K 16/2848 | 435/375 |

(56) References Cited

U.S. PATENT DOCUMENTS

| | | | |
|---|---|---|---|
| 2010/0112068 A1* | 5/2010 | Boyden | A61K 31/00 424/489 |
| 2010/0113614 A1* | 5/2010 | Boyden | A61P 17/02 514/769 |
| 2010/0113615 A1* | 5/2010 | Boyden | A61K 31/00 514/769 |
| 2010/0114348 A1* | 5/2010 | Boyden | A61K 9/0019 700/109 |
| 2010/0114547 A1* | 5/2010 | Boyden | A61K 31/00 703/11 |
| 2010/0119557 A1* | 5/2010 | Boyden | C07K 16/30 435/284.1 |
| 2010/0121466 A1* | 5/2010 | Boyden | C07K 16/283 700/17 |
| 2010/0143243 A1* | 6/2010 | Boyden | A61P 31/16 424/9.4 |
| 2010/0152651 A1* | 6/2010 | Boyden | C07K 16/283 604/113 |
| 2010/0152880 A1* | 6/2010 | Boyden | A61K 38/38 700/283 |
| 2010/0163576 A1* | 7/2010 | Boyden | A61K 9/1641 222/394 |
| 2010/0168900 A1* | 7/2010 | Boyden | A61K 9/1617 700/117 |
| 2010/0185174 A1* | 7/2010 | Boyden | A61K 31/00 604/113 |
| 2010/0187728 A1* | 7/2010 | Boyden | A61K 45/06 264/28 |
| 2010/0249765 A1* | 9/2010 | Johnston | A61B 90/30 606/21 |
| 2010/0274236 A1* | 10/2010 | Krimsky | A61B 17/3211 606/21 |
| 2010/0286791 A1* | 11/2010 | Goldsmith | A61B 17/12022 604/524 |
| 2010/0312084 A1* | 12/2010 | Radojicic | A61M 25/00 604/151 |
| 2011/0150765 A1* | 6/2011 | Boyden | A61K 9/12 424/1.49 |
| 2012/0238936 A1* | 9/2012 | Hyde | A61B 5/1459 604/8 |
| 2013/0296811 A1* | 11/2013 | Bangera | A61B 18/0218 604/290 |
| 2013/0296812 A1* | 11/2013 | Bangera | A61M 35/00 604/290 |
| 2016/0310711 A1* | 10/2016 | Luxon | A61M 1/73 |
| 2017/0122916 A1 | 5/2017 | Leaders | |
| 2017/0136221 A1 | 5/2017 | Budgett | |
| 2017/0173253 A1* | 6/2017 | Funkhouser | A61M 1/3656 |
| 2017/0340801 A1* | 11/2017 | Roger | A61N 1/00 |
| 2020/0188612 A1* | 6/2020 | Brown | A61L 2/04 |
| 2021/0030394 A1* | 2/2021 | Caswell | A61B 1/0052 |
| 2022/0355086 A1* | 11/2022 | Alshareef | G01F 1/662 |
| 2023/0310816 A1* | 10/2023 | Fell | A61B 17/3403 604/8 |

FOREIGN PATENT DOCUMENTS

| | | | | |
|---|---|---|---|---|
| WO | 2018136306 A1 | 7/2018 | | |
| WO | WO-2019118929 A1 * | 6/2019 | | A61B 5/0059 |
| WO | WO-2019195028 A1 * | 10/2019 | | A61B 5/01 |

OTHER PUBLICATIONS

Northwestern University. (Oct. 31, 2018). 'Game-changing' skin sensor could improve life for a million hydrocephalus patients: Band-Aid-like device non-invasively monitors shunt performance in patients with hydrocephalus. 4 pages. ScienceDaily. Retrieved Sep. 8, 2022 from www.sciencedaily.com/releases/2018/10/181031141550.htm.

* cited by examiner

ULTRASOUND-BASED SHUNT FLOW DETECTION

CROSS-REFERENCE TO RELATED APPLICATIONS

This application is the U.S. national phase application filed under 35 U.S.C. § 371 claiming benefit to International Patent Application No. PCT/US2020/058220, filed Oct. 30, 2020, which is entitled to priority under 35 U.S.C. § 119 (e) to U.S. Provisional Patent Application No. 62/928,889 filed on Oct. 31, 2019, each of which application is hereby incorporated herein by reference in its entirety.

BACKGROUND OF THE INVENTION

Ventriculoperitoneal shunts (VPS) are often first line treatments for hydrocephalus. However, these shunts are prone to failure due to partial or complete blockage by cell or protein buildup, bacteria, and blood clots, among others. Shunt failure is difficult to identify as symptoms are ambiguous and nonspecific, such as headache, nausea, vomiting, and changes in vision. Diagnosing shunt failure may require re-operation and shunt exploration to correct and presents further complexity in determining the exact location or locations of blockage.

Certain shunt failure diagnosis methods rely on sensing temperature changes to evaluate shunt flow. For example, external cooling (such as by an ice cube) lowers the temperature of shunt fluid, and changes in temperature are sensed downstream to detect flow. However, these methods and associated devices can only return a binary answer of whether flow is present or absent and cannot assess the degree of flow or the percent of a blockage. Other methods include the use of a tracer injected into a shunt reservoir and microbubble excitation techniques for downstream detection. The tracer method is invasive and defeats the purpose of avoiding an operation, and the latter requires an increased level of sophistication and expertise from an operator.

Thus, there is a need in the art for improved methods and devices for detecting shunt malfunction and degree of shunt blockage. The present invention satisfies this need.

SUMMARY

In one aspect, the present invention relates to a shunt malfunction detection system comprising a shunt malfunction detection device comprising a housing having a sensing end and an ultrasound transducer within the housing aimed towards the sensing end.

In one embodiment, the sensing end comprises an indentation sized to fit over a section of a shunt catheter.

In one embodiment, the housing further comprises a component selected from the group consisting of: a screen, a wireless transceiver, a microprocessor, a memory module, and a power source.

In one embodiment, the system further comprises a pumping device. In one embodiment, the pumping device comprises a housing and an actuation plate. In one embodiment, the actuation plate comprises a bump or other raised element configured to depress a shunt valve and/or reservoir.

In one embodiment, the pumping device further comprises a solenoid connected to the actuation plate, wherein the solenoid is configured to apply a force of actuation to the actuation plate.

In one embodiment, the pumping device further comprises a force sensor connected to the actuation plate and solenoid, wherein the force sensor is configured to measure the force of actuation to the actuation plate.

In one embodiment, the pumping device further comprises a wireless transceiver that is wirelessly linked to the shunt malfunction detection device, such that the shunt malfunction detection device is configured to control a timing, force, and sequence of actuation to the pumping device.

In another aspect, the present invention relates to a method of detecting shunt malfunction, comprising the steps of: providing a shunt detection device having a sensing end with an ultrasound transducer aimed at the sensing end, positioning the shunt detection device over a subject's subcutaneously implanted shunt catheter such that the sensing end is aimed at the catheter, emitting ultrasound waves from the ultrasound transducer towards the catheter, actuating a valve and/or reservoir fluidly connected to the catheter, generating an ultrasound spectrogram from ultrasound waves received by the ultrasound transducer during each actuation of the valve and/or reservoir, performing an analysis of the spectrogram, and determining the location of shunt blockage and/or a percent of shunt blockage based upon the analysis of the spectrogram.

In one embodiment, the analysis of the spectrogram comprises a step selected from the group consisting of: an area under the curve calculation, a wave form analysis, a visual inspection, a fluid velocity analysis, a rate of change analysis, a frequency analysis, an amplitude analysis, and a filtered analysis. In one embodiment, the analysis of the spectrogram is conducted by a user or clinician. In one embodiment, the analysis of the spectrogram is conducted by a computing device. In one embodiment, the computing device utilizes artificial intelligence or machine learning to evaluate the spectrogram.

In one embodiment, the sensing end is aimed at a proximal catheter or a distal catheter of the shunt catheter. In one embodiment, the sensing end is aimed at a portion of the shunt valve. In one embodiment, the actuating step is performed manually. In one embodiment, the actuating step is performed automatically using a pumping device positioned over the valve and/or reservoir.

In one embodiment, the pumping device performs the actuating step using preprogrammed instructions. In one embodiment, the pumping device performs the actuating step using instructions received from the shunt detection device. In one embodiment, the received instructions include actuation force, actuation frequency, and actuation timing. In one embodiment, the received instructions sync actuation with the step of generating an ultrasound spectrogram.

In one embodiment, the method is performed at a time of implanting the shunt catheter to generate a baseline measurement of shunt blockage. In one embodiment, the percent of shunt blockage is determined as a percent difference between the analysis of the spectrogram and the baseline measurement. In one embodiment, the method is performed after the implanting of the shunt catheter. In one embodiment, the method utilizes historical data to determine shunt blockage.

In one embodiment, a percent of shunt blockage between about 0% and 10% indicates no blockage, a percent of shunt blockage between about 11% and 90% indicates a partial blockage, and a percent of shunt blockage between about 91% and 100% indicates a total blockage.

In one embodiment, a percent difference below the baseline measurement indicates a blockage in the shunt catheter that is distal to the position of the shunt detection device. In one embodiment, a percent difference above the baseline measurement indicates a blockage in the shunt catheter that is proximal to the position of the shunt detection device. In one embodiment, the ultrasound spectrogram displays a pattern that corresponds to a blockage type selected from the group consisting of: tissue blockage, blood clot, and catheter kink.

BRIEF DESCRIPTION OF THE DRAWINGS

The following detailed description of exemplary embodiments of the invention will be better understood when read in conjunction with the appended drawings. It should be understood, however, that the invention is not limited to the precise arrangements and instrumentalities of the embodiments shown in the drawings.

FIG. 8A through FIG. 8C depict the results of the experimental setup in FIG. 5 simulating normal shunt flow and shunt malfunction.

DETAILED DESCRIPTION

The present invention provides devices and systems for detecting shunt malfunction. The detection devices employ ultrasound instrumentations to evaluate shunt malfunction. The detection devices can be coupled with pumps to provide consistent shunt valve and/or reservoir actuation for reliable readings. The devices can output a determination of a degree of shunt blockage and relative location of shunt blockage.

Definitions

It is to be understood that the figures and descriptions of the present invention have been simplified to illustrate elements that are relevant for a clear understanding of the present invention, while eliminating, for the purpose of clarity, many other elements typically found in the art. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art.

Unless defined elsewhere, all technical and scientific terms used herein have the same meaning as commonly understood by one of ordinary skill in the art to which this invention belongs. Although any methods and materials similar or equivalent to those described herein can be used in the practice or testing of the present invention, the exemplary methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20%, ±10%, ±5%, ±1%, and ±0.1% from the specified value, as such variations are appropriate.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6, etc., as well as individual numbers within that range, for example, 1, 2, 2.7, 3, 4, 5, 5.3, 6, and any whole and partial increments there between. This applies regardless of the breadth of the range.

In some aspects of the present invention, software executing the instructions provided herein may be stored on a non-transitory computer-readable medium, wherein the software performs some or all of the steps of the present invention when executed on a processor.

Aspects of the invention relate to algorithms executed in computer software. Though certain embodiments may be described as written in particular programming languages, or executed on particular operating systems or computing platforms, it is understood that the system and method of the present invention is not limited to any particular computing language, platform, or combination thereof. Software executing the algorithms described herein may be written in any programming language known in the art, compiled or interpreted, including but not limited to C, C++, C#, Objective-C, Java, JavaScript, Python, PHP, Perl, Ruby, or Visual Basic. It is further understood that elements of the present invention may be executed on any acceptable computing platform, including but not limited to a server, a cloud instance, a workstation, a thin client, a mobile device, an embedded microcontroller, a television, or any other suitable computing device known in the art.

Parts of this invention are described as software running on a computing device. Though software described herein may be disclosed as operating on one particular computing device (e.g. a dedicated server or a workstation), it is understood in the art that software is intrinsically portable and that most software running on a dedicated server may also be run, for the purposes of the present invention, on any of a wide range of devices including desktop or mobile devices, laptops, tablets, smartphones, watches, wearable electronics or other wireless digital/cellular phones, televisions, cloud instances, embedded microcontrollers, thin client devices, or any other suitable computing device known in the art.

Similarly, parts of this invention are described as communicating over a variety of wireless or wired computer networks. For the purposes of this invention, the words "network", "networked", and "networking" are understood to encompass wired Ethernet, fiber optic connections, wireless connections including any of the various 802.11 standards, cellular WAN infrastructures such as 3G or 4G/LTE networks, Bluetooth®, Bluetooth® Low Energy (BLE) or Zigbee® communication links, or any other method by which one electronic device is capable of communicating with another. In some embodiments, elements of the networked portion of the invention may be implemented over a Virtual Private Network (VPN).

Shunt Malfunction Detection Device

The present invention provides devices and systems that evaluate suspected shunt malfunction. The devices and systems lower the heavy cost burden related to shunt malfunction and reduce the amount of radiation and number of invasive procedures to which patients are subjected. In some embodiments, the devices and systems utilize an ultrasound-based algorithm to evaluate shunt malfunction.

Figure 1:
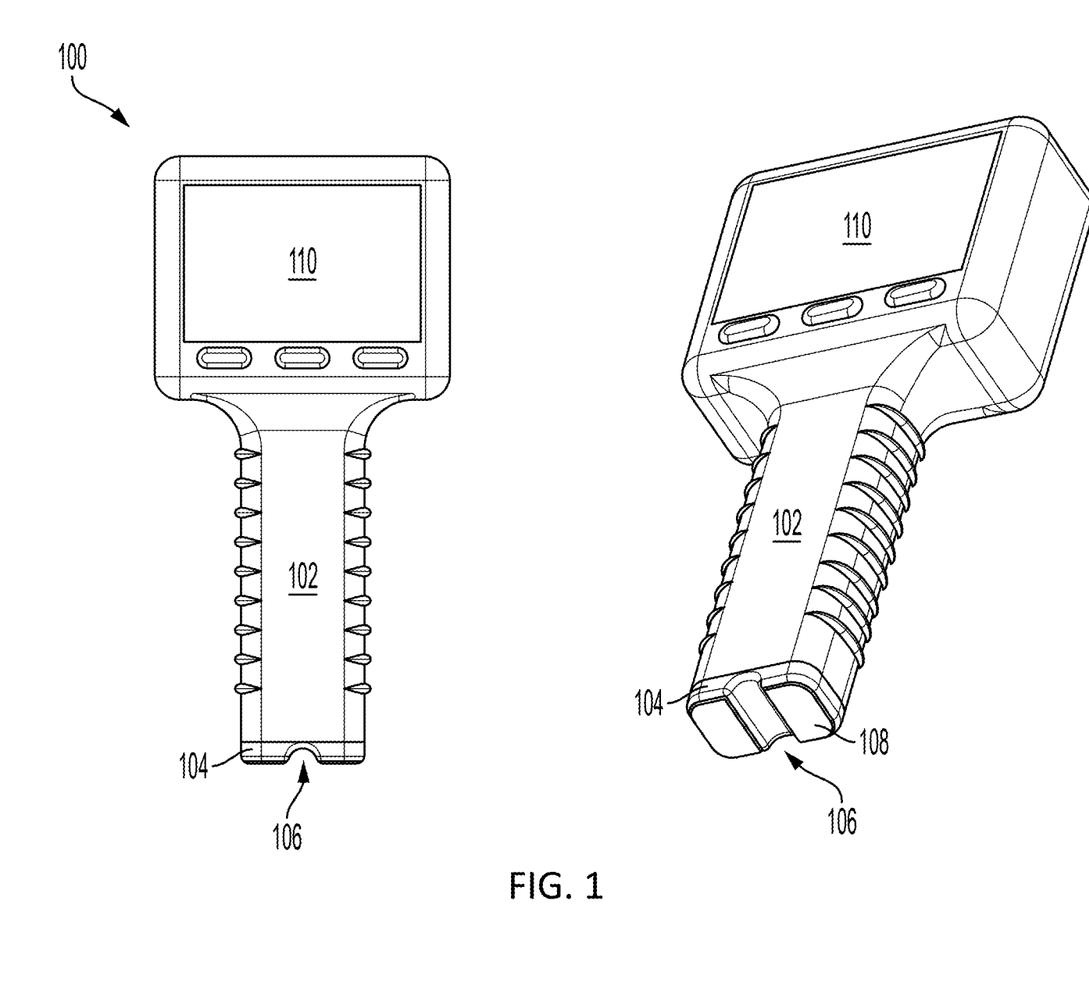
FIG. 1 depicts a front view (left) and a perspective view (right) of an exemplary shunt malfunction detection device.

Referring now to FIG. 1, an exemplary shunt malfunction detection device 100 is now described. Device 100 comprises a housing 102 having a sensing end 104. Sensing end 104 may further comprise one or more indentations adapted to fit medical tubing, valves, or the anatomical structures of a patient. Specifically, the one or more indentations may be adapted to fit shunt tubing, shunt valve or reservoir, or may run perpendicular to shunt tubing and be adapted to fit a collarbone of a patient. FIG. 1 demonstrates one such possible configuration and comprises an indentation 106 and pads 108 positioned on opposing sides of indentation 106. In some embodiments, device 100 further comprises a screen 110. In some embodiments, screen 110 may be separate from device 100, and device 100 may possess wired or wireless means to communicate with screen 110.

Figure 2:
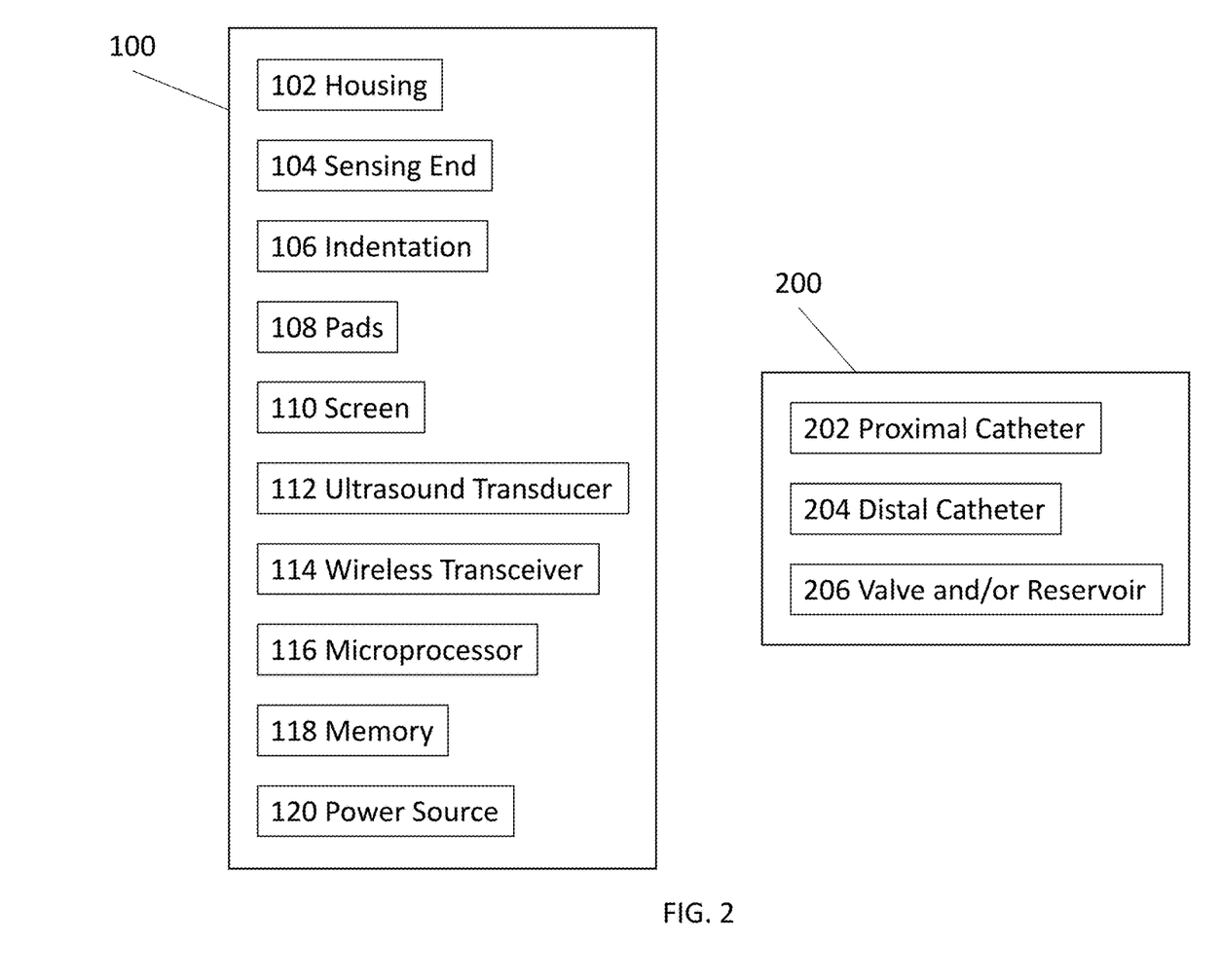
FIG. 2 is a box diagram of an exemplary shunt malfunction detection system.

Referring now to FIG. 2, a block diagram is depicted listing further potential components of device 100 and a complementary shunt 200 that may or may not be included in the device and system. As shown in the block diagram, device 100 can further comprise an ultrasound transducer 112, wireless transceiver 114, microprocessor 116, memory 118, and power source 120. In various embodiments, device 100 can further include one or more human interface input elements, including but not limited to buttons, switches, knobs, dials, touch-sensitive capacitive or resistive sensors, and the like. Shunt 200 can comprise any of the following elements: a proximal catheter 202, a distal catheter 204, and a valve and/or reservoir 206 joining proximal catheter 202 and distal catheter 204.

Device 100 detects blockage within an implanted shunt by directing ultrasound waves towards a shunt catheter to detect fluid movement within the shunt catheter. In one embodiment, the ultrasound waves from the ultrasound transducer 112 are configured to penetrate about 2-5 mm under the skin. In some embodiments the ultrasound transducer 112 may be linear, curvilinear or phased area. In one embodiment, ultrasound transducer 112 is a Doppler probe. In some embodiments the ultrasound transducer 112 can utilize color Doppler, power Doppler, spectral Doppler, duplex Doppler or continuous wave Doppler. In one embodiment, device 100 utilizes the Doppler Effect to detect fluid movement and direction of fluid flow. Device 100 thereby comprises ultrasound transducer 112 aimed towards sensing end 104. Sensing end 104 comprises a sonolucent material. In some embodiments, sensing end 104 is removable and disposable, such that a used sensing end 104 can be exchanged for a sterile sensing end 104 prior to each use. In certain embodiments, sensing end 104 can comprise a non-slip surface provided by pads 108 constructed from a gel or rubber material. In certain other embodiments, sensing end 104 comprises indentation 106 positioned between each pad 108, wherein indentation 106 is sized to accommodate the dimensions of a section of a shunt catheter. In certain other embodiments, sensing end 104 is removable and shaped to accommodate existing ultrasound and ultrasonic devices.

Microprocessor 116 may be configured to read and process data from ultrasound transducer 112. In some embodiments, device 100 comprises machine-readable software instructions on a non-transitory computer-readable medium (such as memory 118), the instructions comprising one or more control and/or data analysis algorithms. In some embodiments, the algorithms include machine learning and/or artificial intelligence algorithms that improves the analysis and determination of shunt blockage based on input data over time.

In some embodiments, certain control elements of device 100 are performed by a microprocessor 116 disposed within housing 102, while other control elements are performed remote from device 100 by a second computing device or set of computing devices. In some embodiments, one or more computing devices remote from device 100 receive data from ultrasound transducer 112, perform one or more calculations, and transmit instructions back to microprocessor 116 disposed within device 100. Microprocessor 116 may comprise or be communicatively connected to one or more wired or wireless communication links through wireless transceiver 114, including WiFi, Bluetooth, cellular data connections, Near-Field communication (NFC), or the like.

In some embodiments, the devices of the present invention may operate in conjunction with a computer platform system, such as a local or remote executable software platform, or as a hosted internet or network program or portal. In certain embodiments, portions of the system may be computer operated, or in other embodiments, the entire system may be computer operated. As contemplated herein, any computing device as would be understood by those skilled in the art may be used with the system, including desktop or mobile devices, laptops, desktops, tablets, smartphones or other wireless digital/cellular phones, televisions or other thin client devices as would be understood by those skilled in the art.

The computer platform is fully capable of sending and interpreting device emissions signals as described herein throughout. For example, the computer platform can be configured to control emissions parameters such as frequency, intensity, amplitude, period, wavelength, pulsing, and the like, depending on the emissions type. The computer platform can also be configured to control the actuation of the device, such as angulation and partial locking. The computer platform can be configured to record received emissions signals, and subsequently interpret the emissions. For example, the computer platform may be configured to interpret the emissions as images and subsequently transmit the images to a digital display. The computer platform may further perform automated calculations based on the received emissions to output data such as density, distance, temperature, composition, imaging, and the like, depending on the type of emissions received. The computer platform may further provide a means to communicate the received emissions and data outputs, such as by projecting one or more static and moving images on a screen, emitting one or more auditory signals, presenting one or more digital readouts, providing one or more light indicators, providing one or more tactile responses (such as vibrations), and the like. In some embodiments, the computer platform communicates received emissions signals and data outputs in real time, such that an operator may adjust the use of the device in response to the real time communication. For example, in response to a stronger received emission, the computer platform may output a more intense light indicator, a louder auditory signal, or a more vigorous tactile response to an operator, such that the operator may adjust the device to receive a stronger signal or the operator may partially lock the device in a position that registers the strongest signal. In a further example, the computer platform may display image overlays to represent an inserted medical device in relation to a displayed ultrasound image or volume rendering (3D reconstruction) on screen.

In some embodiments, the computer platform is integrated into the devices of the present invention. For example, in some embodiments, at least one component of the computer platform described elsewhere herein is incorporated into a shunt malfunction detection device of the present invention, such as emissions parameter controlling means, emissions recording and interpretation means, communication means for the received emissions and data outputs, and one or more features for displaying the received emissions, data, and images. Shunt malfunction detection devices having at least one integrated computer platform component may be operable as a self-contained unit, such that additional computer platform components apart from the device itself are not necessary. Self-contained units provide a convenient means of using the devices of the present invention by performing a plurality of functions related to the devices. Self-contained units may be swappable and disposable, improving portability and decreasing the risk of contamination.

The computer operable component(s) may reside entirely on a single computing device, or may reside on a central server and run on any number of end-user devices via a communications network. The computing devices may include at least one processor, standard input and output devices, as well as all hardware and software typically found on computing devices for storing data and running programs, and for sending and receiving data over a network, if needed. If a central server is used, it may be one server or, more preferably, a combination of scalable servers, providing functionality as a network mainframe server, a web server, a mail server and central database server, all maintained and managed by an administrator or operator of the system. The computing device(s) may also be connected directly or via a network to remote databases, such as for additional storage backup, and to allow for the communication of files, email, software, and any other data formats between two or more computing devices. There are no limitations to the number, type or connectivity of the databases utilized by the system of the present invention. The communications network can be a wide area network and may be any suitable networked system understood by those having ordinary skill in the art, such as, for example, an open, wide area network (e.g., the internet), an electronic network, an optical network, a wireless network, a physically secure network or virtual private network, and any combinations thereof. The communications network may also include any intermediate nodes, such as gateways, routers, bridges, internet service provider networks, public-switched telephone networks, proxy servers, firewalls, and the like, such that the communications network may be suitable for the transmission of information items and other data throughout the system.

The software may also include standard reporting mechanisms, such as generating a printable results report, or an electronic results report that can be transmitted to any communicatively connected computing device, such as a generated email message or file attachment. Likewise, particular results of the aforementioned system can trigger an alert signal, such as the generation of an alert email, text or phone call, to alert a manager, expert, researcher, or other professional of the particular results. Further embodiments of such mechanisms are described elsewhere herein or may standard systems understood by those skilled in the art.

Screen 110 can be used to display ultrasonography readings from ultrasound transducer 112 for interpretation as well as a diagnostic result output by microprocessor 116 and stored on memory 118, such as a message indicating blockage, no blockage, or a percent blockage, and whether a blockage is proximal or distal to a valve and/or reservoir. Screen 110 can also be used to display accurate placement of device 100 over a shunt catheter, to display device settings for selection and modification, and to display manuals, directions, and timers to aid in operating device 100. Additionally, any information that can be displayed by screen 110 can also be displayed by any screen that is in communication with device 100. The various components of device 100 can be powered by power source 120, such as a rechargeable battery, non-rechargeable battery, or electrical plugin.

Device 100 is configured to diagnose shunt malfunction by analyzing flow rate of fluid through shunt tubing. One such method of diagnosing shunt malfunction is by timing ultrasound pulses with actuation of an implanted shunt valve and/or reservoir and detecting fluid flow within an implanted shunt catheter. While valve and/or reservoir actuation may be performed manually, the present invention also provides a pumping device 300 that performs consistent actuation, shown in FIG. 3. In one embodiment, pumping device 300 comprises a locating device 302 and an inner actuation plate 304 having a raised element such as bump 306. Locating device 302 can possess some means of attaching a pumping mechanism (such as actuation plate 304) to a patient including, but not limited to, Velcro straps, adhesives, suction, or any other mechanical or chemical means of attachment. In one embodiment, bump 306 is accessible and visible through optional window 308 on locating device 302. Locating device 302 can be attached to a subject and positioned such that bump 306 rests against a shunt valve and/or reservoir. Suction cup 302 can be pressed to push actuation plate 304 and bump 306 towards the shunt valve and/or reservoir, whereupon bump 306 presses against the shunt valve and/or reservoir to move fluid through a shunt catheter. Actuation plate 304 provides a rigid platform to stably receive a pressing force such that bump 306 can be consistently actuated towards the shunt valve and/or reservoir for substantially the same distance and to apply substantially the same force for each actuation.

Figure 3:
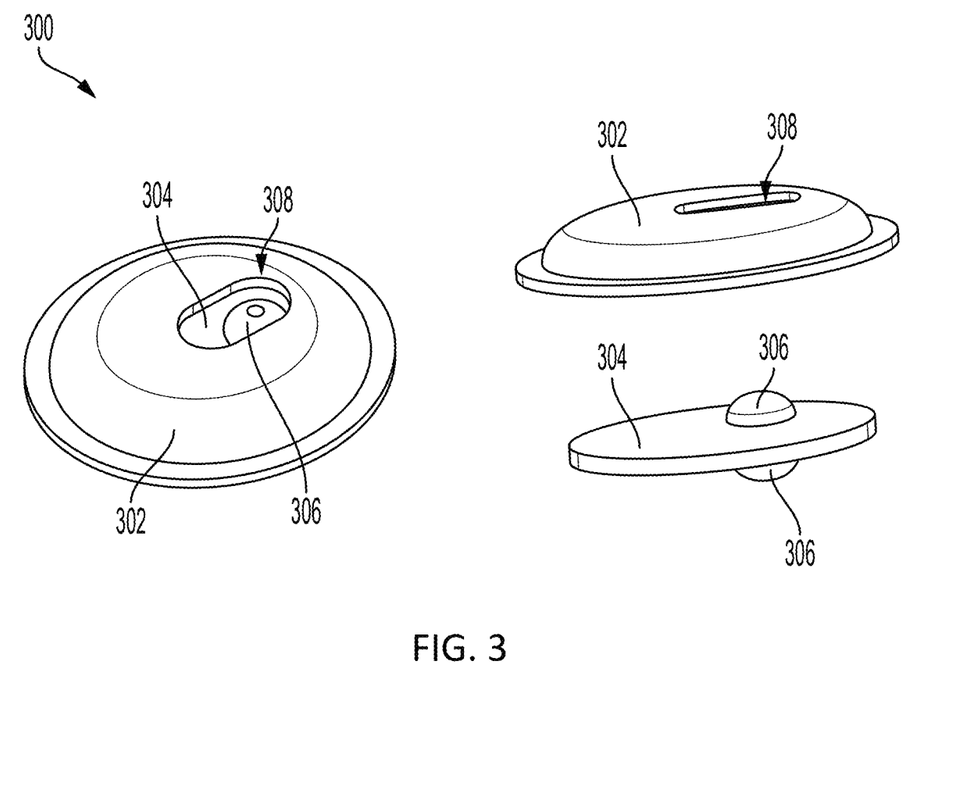
FIG. 3 depicts a perspective view (left) and an exploded view (right) of an exemplary pumping device.

It should be understood that pumping devices useful within the scope of the present invention are not limited to the depiction in FIG. 3. In some embodiments, the pumping devices employ a spring-loaded button, wherein the spring provides a consistent force of actuation. In some embodiments, the pumping devices employ a solenoid, wherein the solenoid is preprogrammed to provide a consistent force of actuation. In other embodiments, the pumping devices employ a servo or other actuator to provide consistent force of actuation.

In various embodiments, the pumping devices comprise a wireless transceiver powered by a power source, wherein the wireless transceiver can be wirelessly connected to wireless transceiver 114 of device 100. In some embodiments, the pumping devices can include a force or pressure sensor that detects and measures feedback from the valve and/or reservoir after actuation. Device 100 can thereby control the timing of actuating the pumping devices, the force of actuation, and a sequence of actuation. By controlling the timing, force, and sequence of actuation, device 100 can coordinate each valve and/or reservoir actuation with ultrasound pulses to detect fluid flow.

In one example embodiment, the actuator comprises an integrated force sensor to enable the system to understand the pressure related to an actuation of the shunt valve. Additionally, the integrated force sensor can provide information for the algorithm to analyze an occlusion. In one embodiment, the actuator is a handheld device. In another embodiment the actuator is a wearable device. Examples of the wearable device can include a thumb sleeve, glove, arm band, head band, cap, or other suitable wearable devices known to experts in the art.

In one example embodiment, a Python based GUI is utilized to; manually control the actuator, provide an interface to specify/save/load the actuator protocol, tabulate and visualize the audio data, perform basic analysis of the audio date and export the data and a summary of the results. The above mentioned is merely an example and should not be read as limiting. Other suitable control software implementation schemes can be utilized to perform the same or similar functions.

In one example embodiment, the actuator is a HiTec D941TW Servo. In one example embodiment the doppler is a Huntleigh MD2 Dopplex. In one example embodiment the doppler is an IPP3 probe. In one example embodiment the doppler is an EZ8 probe. In one example embodiment the compute and control platform can include a Raspberry Pi 4 model B Desktop Kit, a Raspberry Pi Capacitive Touch Screen, a USB Audio Capture Device, and a USB to RS232 Converter or GPIO converter. The above mentioned components are merely an example and should not be read as limiting. Other suitable components can be utilized to perform the same or similar functions.

The devices of the present invention can be made using any suitable method known in the art. The method of making may vary depending on the materials used. For example, devices substantially comprising a metal may be milled from a larger block of metal or may be cast from molten metal. Likewise, components substantially comprising a plastic or polymer may be milled from a larger block, cast, or injection molded. In some embodiments, the devices may be made using 3D printing or other additive manufacturing techniques commonly used in the art.

Methods of Detecting Shunt Malfunction

The present invention also includes methods of detecting shunt malfunction. As described elsewhere herein, the devices and systems of the present invention couple ultrasonography with shunt valve and/or reservoir actuation to determine shunt blockage location and percentage. In one embodiment of the method the ultrasonography is Doppler ultrasonography. In some embodiments, the method of ultrasonography is one of color Doppler, power Doppler, spectral Doppler, duplex Doppler or continuous wave Doppler.

Ventriculoperitoneal shunts are typically implanted with a proximal catheter extending into ventricles of the brain in need of drainage, a distal catheter extending into a body cavity or organ for removing excess cerebrospinal fluid, and a valve and/or reservoir connecting the proximal catheter to the distal catheter. The valve and/or reservoir and a section of the proximal catheter and the distal catheter are implanted subcutaneously and can be located by touch or other means of detection. The lengths of the catheters that are positioned just under the skin can be accessed noninvasively by the devices and systems of the present invention to detect shunt malfunction.

Figure 4:
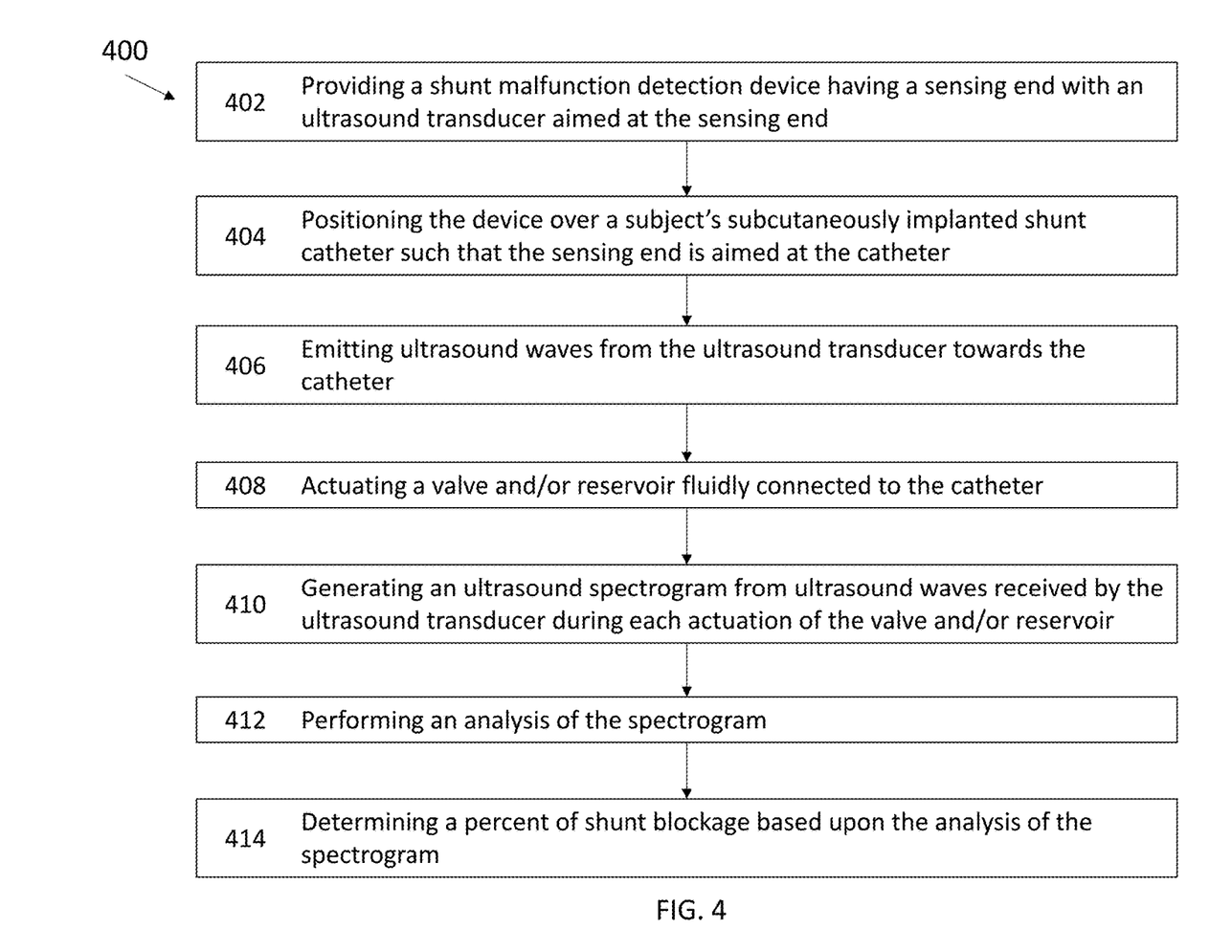
FIG. 4 is a flowchart of an exemplary method of detecting shunt malfunction.

Referring now to FIG. 4, an exemplary method 400 of detecting shunt malfunction is depicted. In step 402, a shunt malfunction detection device is provided, the device having a sensing end with an ultrasound transducer aimed at the sensing end. In some embodiments, the shunt malfunction detection device is device 100 described elsewhere herein. In some embodiments, the device can be any suitable ultrasound device commonly used in the art. In step 404, the device is positioned over a subject's subcutaneously implanted shunt catheter such that the sensing end is aimed at the catheter. A device such as device 100 of the present invention permits a catheter to be aligned within an indentation of device 100. Likewise, the addition of sensing end 104 to any suitable ultrasound device permits a catheter to be aligned within an indentation of device 100. In step 406, ultrasound waves are emitted from the ultrasound transducer towards the catheter. In step 408, a valve and/or reservoir fluidly connected to the catheter is actuated. In some embodiments, an initial test actuation or a priming actuation is performed. In step 410, an ultrasound spectrogram is generated from ultrasound waves received by the ultrasound transducer during each actuation of the valve and/or reservoir. In step 412, an analysis of the resultant spectrogram is performed. The analysis can be any suitable visual analysis or mathematical calculation sufficient to analyze variations in the spectrogram, including but not limited to: area under the curve calculation, a wave form analysis, visual inspection, fluid velocity analysis, rate of change analysis, frequency analysis, amplitude analysis, filtered analysis, or any other mathematical means. The analysis can be conducted by the user or clinician. In one embodiment, the analysis is conducted by a computing device. For example, the analysis can be conducted by the device of the present invention, as described elsewhere herein, or by one or more remote computing devices. Exemplary computing devices include, but is not limited to, desktop or mobile devices, laptops, desktops, tablets, smartphones or other wireless digital/cellular phones, televisions or other thin client devices as would be understood by those skilled in the art. In one embodiment, the computing device utilizes machine learning or Artificial Intelligence to conduct the analysis. In step 414, a percent of shunt blockage is determined based upon the analysis (e.g., visual inspection or mathematical calculation) of the spectrogram.

The device can be positioned over a section of the distal catheter, a section of the proximal catheter, or over a section of valve and/or reservoir. In one embodiment, the sensing end is aimed at a proximal catheter or a distal catheter of the shunt catheter. In one embodiment, the sensing end is aimed at a portion of the shunt valve. In some embodiments, the actuating step is performed manually by hand or with a provided pumping device positioned over the valve and/or reservoir. In some embodiments, the actuating step is performed automatically by a provided pumping device positioned over the valve and/or reservoir. Automatic actuation can be done by a pumping device having preprogrammed instructions or by a pumping device receiving instructions from the device, wherein the instructions can include actuation force, actuation frequency, and actuation timing, and wherein the instructions coordinate or sync actuation with signal recording. For example, the instructions can provide for a series of ten valve and/or reservoir actuations over a time period of 30 seconds, such that each actuation is spaced apart by 3 seconds. The instructions would thereby coordinate the device to record each 3 second interval as a separate actuation instance and thereby output ten calculations for each instance.

The visual inspection or mathematical calculation is assessed against a baseline measurement that corresponds to unobstructed shunt flow to determine shunt blockage. In some embodiments, a baseline measurement is measured for each subject at the time of shunt implantation and stored on memory, such as memory 118 of a device 100. In some embodiments, a baseline measurement is created from an average of baseline measurements measured from a plurality of subjects at the time of shunt implantation. In some embodiments, a baseline measurement is measured using a shunt catheter simulating fluid drainage. In some embodiments, the baseline measurement is established via machine learning or Artificial Intelligence. In some embodiments, the baseline measurement is a range between about 3500 and 5500.

In one embodiment, the method is performed after the implanting of the shunt catheter. In one embodiment, the method utilizes historical data to determine shunt blockage.

In some embodiments, a mathematical calculation that is equal to or within about 10% of a baseline measurement indicates no blockage. In some embodiments, a mathematical calculation that is less than a baseline measurement indicates distal occlusion. In some embodiments, a mathematical calculation that is greater than a baseline measurement indicates proximal occlusion. Percent blockage can be determined as a ratio of a mathematical calculation against a baseline measurement. For example, a mathematical calculation that is about 40% less than a baseline measurement can be interpreted as about a 40% distal blockage, while a mathematical calculation that is about 40% more than a baseline measurement can be interpreted as about a 40% proximal blockage. In some embodiments, the percent of shunt blockage can be interpreted as a general indicator of whether a blockage is present or absent. For example, a range of between about 0% to 10% can be interpreted as no blockage, a range of between about 11% and 90% can be interpreted as partial blockage, and a range of between about 91% and 100% can be interpreted as total blockage.

In certain embodiments, the ultrasound spectrograph can be used to determine the type of shunt blockage. For example, different ultrasound spectrographs can possess similar mathematical calculations but vary in terms of amplitude and frequency. Amplitude and frequency of the ultrasound spectrographs can form identifiable patterns that correspond to certain types of shunt blockage, including but not limited to tissue blockage, blood clots, catheter kinks, and the like. In certain embodiments, data from ultrasound spectrographs can be utilized to train machine learning algorithms and/or Artificial Intelligence to determine different types of shunt blockage.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out exemplary embodiments of the present invention, and are not to be construed as limiting in any way the remainder of the disclosure.

Example 1

Demonstration of Shunt Malfunction Doppler Ultrasonography

Figure 5:
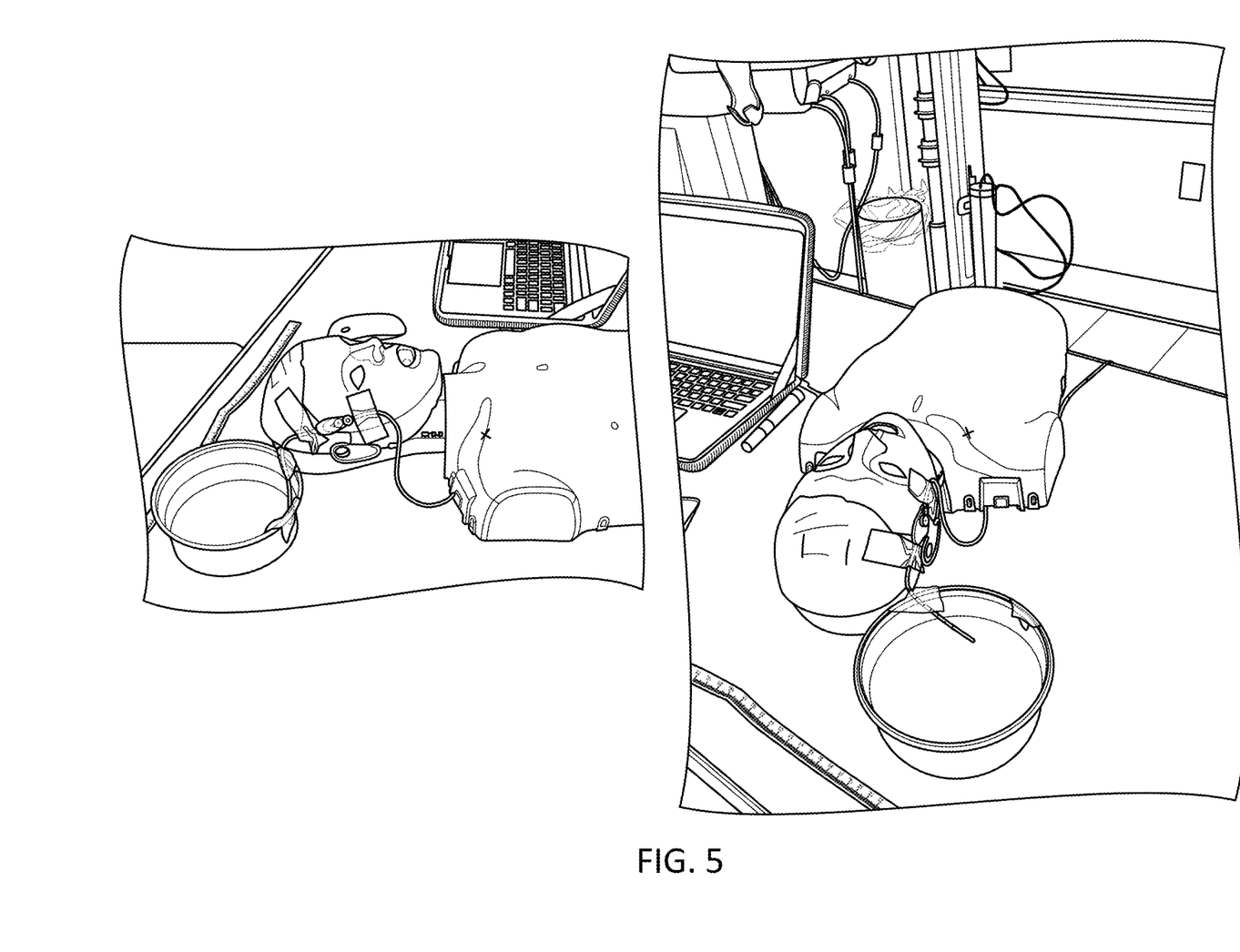
FIG. 5 depicts an experimental setup of a shunt malfunction simulation.
Figure 6A:
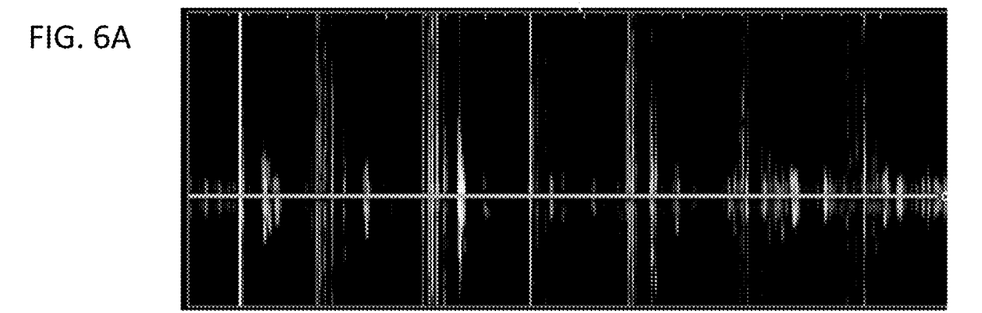
FIG. 6A through FIG. 6D depict Doppler sonograms of the experimental setup in FIG. 5 simulating normal shunt flow (FIG. 6A), 50% distal shunt occlusion (FIG. 6B), 75% distal shunt occlusion (FIG. 6C), and 100% distal shunt occlusion (FIG. 6D).
Figure 6B:
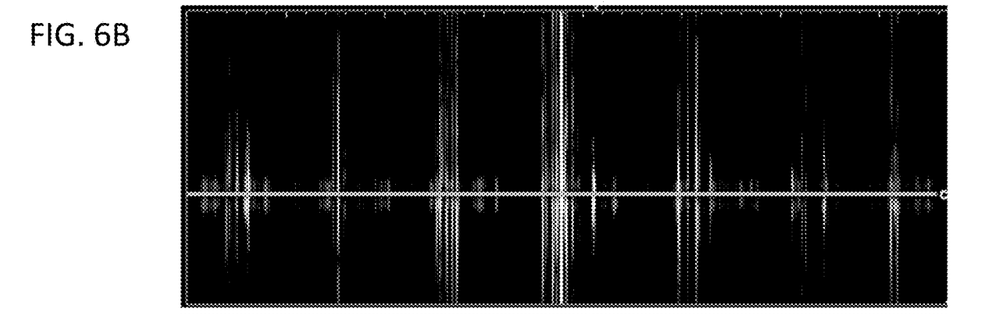
Figure 6C:
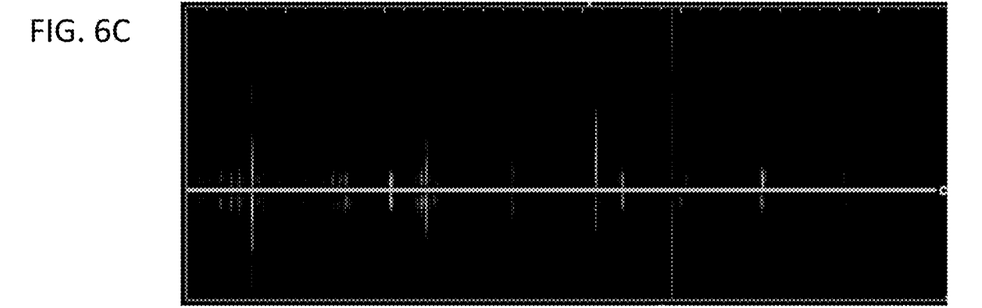
Figure 6D:
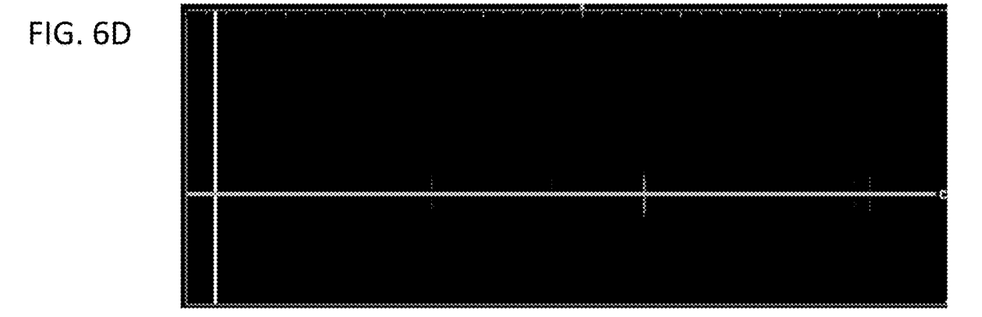
Figure 7A:
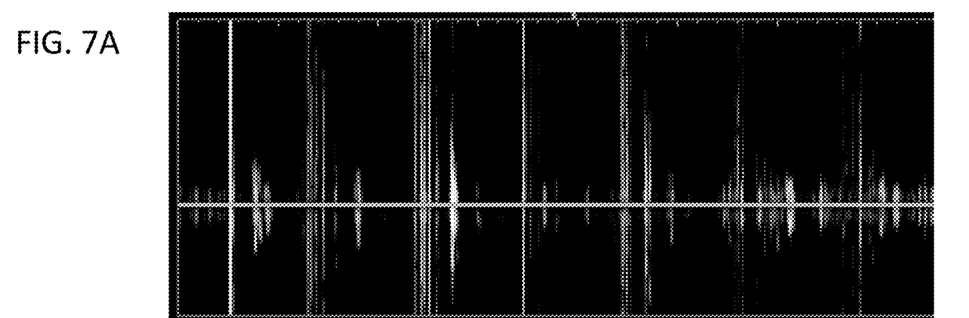
FIG. 7A through FIG. 7D depict Doppler sonograms of the experimental setup in FIG. 5 simulating normal shunt flow (FIG. 7A), 50% proximal shunt occlusion (FIG. 7B), 75% proximal shunt occlusion (FIG. 7C), and 100% proximal shunt occlusion (FIG. 7D).
Figure 7B:
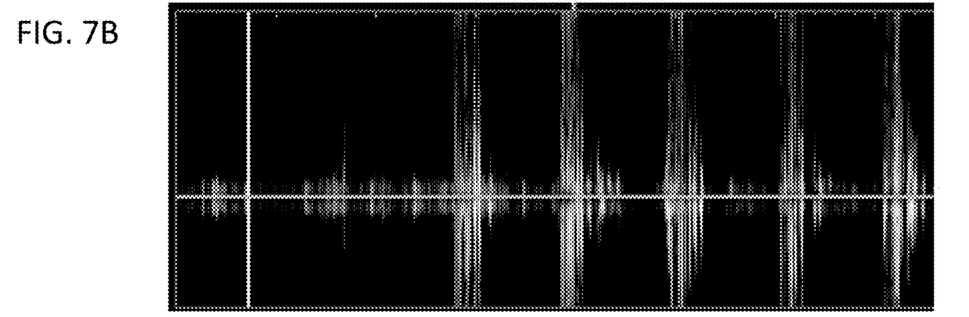
Figure 7C:
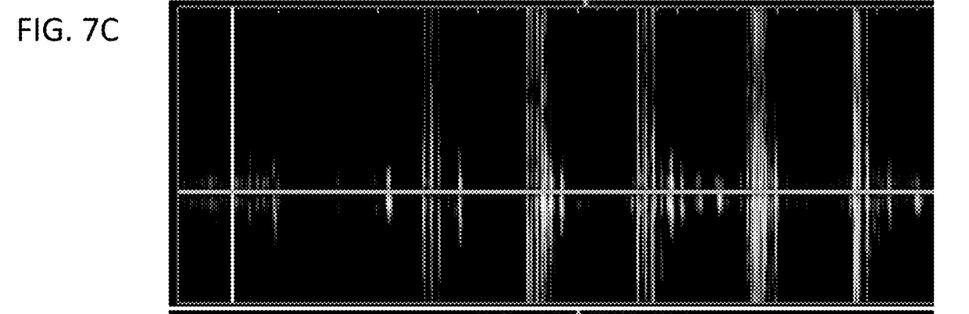
Figure 7D:
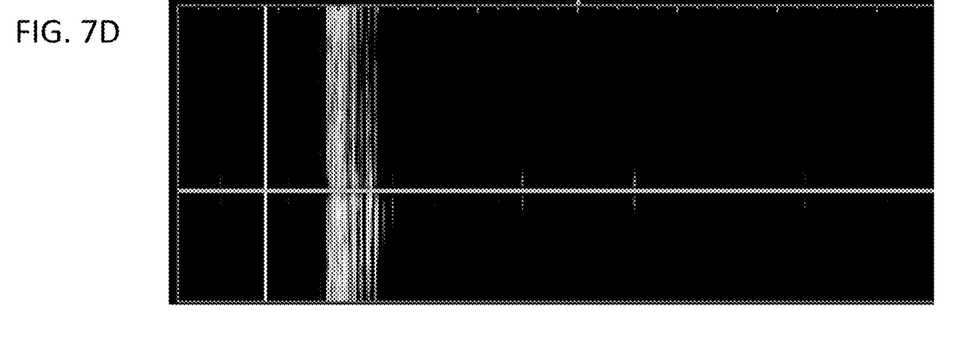
Figure 8A:
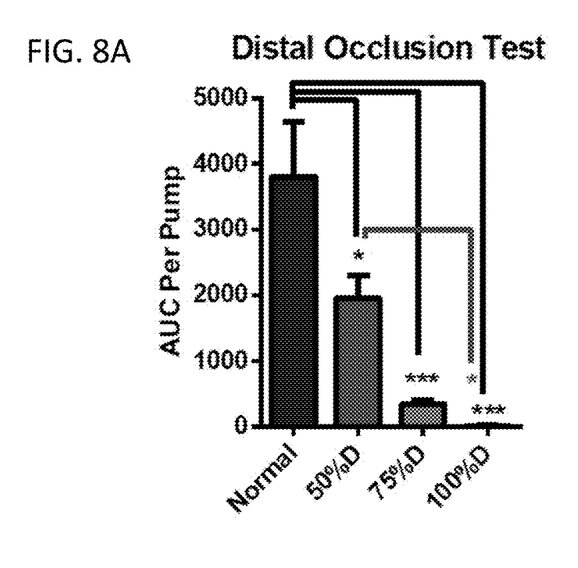
FIG. 8A is a bar graph of the results of the distal occlusion test.
Figure 8B:
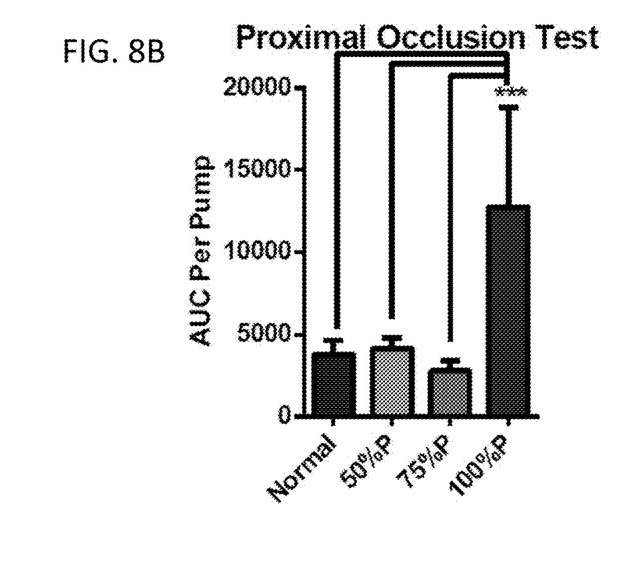
FIG. 8B is a bar graph of the results of the proximal occlusion test.
Figure 8C:
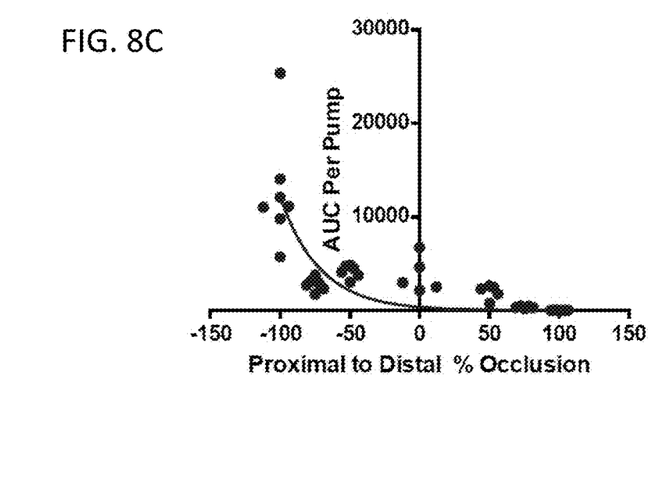
FIG. 8C is a graph approximating proximal to distal percent occlusion.

An experimental setup of a shunt catheter with a valve and/or reservoir is shown in FIG. 5. In this particular experiment, Doppler ultrasound was employed, although any form of ultrasonic detection may be utilized. The valve and/or reservoir was pumped in sync with ultrasound sonography to generate the Doppler spectrographs shown in FIG. 6A through FIG. 6D and FIG. 7A through FIG. 7D. FIG. 6A through FIG. 6D simulated distal shunt occlusion wherein FIG. 6A had no occlusion, FIG. 6B had 50% occlusion, FIG. 6C had 75% occlusion, and FIG. 6D had total occlusion. FIG. 7A through FIG. 7D simulated proximal shunt occlusion wherein FIG. 7A had no occlusion, FIG. 7B had 50% occlusion, FIG. 7C had 75% occlusion, and FIG. 7D had total occlusion. In this particular experiment, an area under the curve calculation was performed for FIG. 6A through FIG. 6D and FIG. 7A through FIG. 7D as shown in FIG. 8A and FIG. 8B, respectively, although any suitable visual inspection or mathematical calculation may be employed to analyze the output of the ultrasound sonography. A compilation of several measurements at each level of proximal and distal occlusion is shown in FIG. 8C The qualitative difference in signal from normal shunt to partial proximal, distal, and complete proximal and distal obstructions in the spectrographs is apparent. Furthermore, after obtaining the area under the curve (AUC), essentially evaluating acceleration per pump, a statistical significance was found in the difference between normal and all patterns of distal obstruction. Statistical significance was also found between normal shunt flow and proximal occlusion, without significance in partial proximal occlusions. Based on the concepts in the Navier-Stokes momentum equation for incompressible liquids, the prediction that a high amplitude would be detected distally if there is a proximal occlusion and vice versa was proven.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A shunt malfunction detection system, comprising:
a shunt malfunction detection device comprising a housing having a sensing end with an indentation sized to fit over a section of a subcutaneously implanted shunt; and
an ultrasound transducer within the housing aimed towards the sensing end.

2. The system of claim 1, wherein the ultrasound transducer is a Doppler ultrasound transducer.

3. The system of claim 1, wherein the housing further comprises a component selected from the group consisting of: a screen, a wireless transceiver, a microprocessor, a memory module, and a power source.

4. The system of claim 1, wherein the system further comprises a pumping device.

5. The system of claim 4, wherein the pumping device comprises a housing and an actuation plate, wherein the actuation plate comprises a bump or raised element configured to depress a shunt valve and/or reservoir.

6. The system of claim 2, wherein the system further comprises a pumping device comprising a housing and an actuation plate, wherein the actuation plate comprises a bump or raised element configured to depress a shunt valve and/or reservoir.

7. The system of claim 5, wherein the pumping device further comprises a solenoid connected to the actuation plate, wherein the solenoid is configured to apply a force of actuation to the actuation plate.

8. The system of claim 7, wherein the pumping device further comprises a force sensor connected to the actuation plate and solenoid, wherein the force sensor is configured to measure the force of actuation to the actuation plate.

9. The system of claim 8, wherein the pumping device further comprises a wireless transceiver that is wirelessly linked to the shunt malfunction detection device, such that the shunt malfunction detection device is configured to control a timing, force, and sequence of actuation to the pumping device.

* * * * *